United States Patent
Hidaka et al.

(12)

(10) Patent No.: US 6,294,633 B1
(45) Date of Patent: Sep. 25, 2001

(54) CATALYSTS FOR PRODUCING METHYLAMINES

(75) Inventors: Toshio Hidaka; Katsumi Higuchi, both of Tsukuba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/630,559

(22) Filed: Aug. 2, 2000

(30) Foreign Application Priority Data

Aug. 3, 1999 (JP) .................................................. 11-220049

(51) Int. Cl.$^7$ .................................................. C07C 209/16
(52) U.S. Cl. ........................ 526/908; 564/479; 564/480; 564/486
(58) Field of Search ................................... 564/479, 480, 564/486; 526/908

(56) References Cited

U.S. PATENT DOCUMENTS 4,313,003 * 1/1982 Weigert ................................ 564/463

OTHER PUBLICATIONS

Database CAPLUS on STN, Acc. No. 1998:773080 QIU et al., 'Selective synthesis of dimethylamine over rare earth modified mordenites.' J. Nat. Gas Chem. (1998), 7(4), pp. 297–305 (abstract).*

* cited by examiner

Primary Examiner—Johann Richter
Assistant Examiner—Brian J. Davis
(74) Attorney, Agent, or Firm—Fitch, Even, Tabin & Flannery

(57) ABSTRACT

Catalysts for producing methylamines are provided, which comprise mordenite, as the essential component, of spherical fine particles having a crystal diameter of not more than 0.5 $\mu$m. When the catalysts are used for the production of dimethylamine from methanol and ammonia or through a disproportionation of methylamines, they exhibit a high dimethylamine productivity with the formation of few amount of trimethylamine whose demand is very small. The process can be operated for a long period of time without decrease in the catalyst activity.

8 Claims, 1 Drawing Sheet

CATALYSTS FOR PRODUCING METHYLAMINES

BACKGROUND OF THE INVENTION

1. Field of the Invention

The present invention relates to catalysts for producing methylamines. The catalysts have superior performances in the production of methylamines from methanol and ammonia, or through a disproportionation reaction of monomethylamine. Methylamines, including dimethylamine are used as materials for solvents such as dimethylformamide, rubber products, pharmaceuticals, surfactants, and others.

2. Description of the Prior Art

Methylamines are usually produced from methanol and ammonia in the presence of solid acid catalysts such as silica-alumina, at a temperature of approximately 400° C. Alternatively, methylamines are produced through a disproportionation reaction of monomethylamine. The productions of methylamines as mentioned above produce mainly trimethylamine which is of little use from a commercial point of view. A selective production method of dimethylamine has long been earnestly desired, because demands for methylamines are directed to dimethylamine.

There are proposed a few methods for producing methylamines using zeolite catalysts which are more advantageous over the previous silica-alumina catalysts; for example, methods which use zeolite A (JP 56-69846 A), FU-1 (JP 54-148708 A), ZSM-5 (U.S. Pat. No. 4,082,805), ferrierite and erionite (JP 56-113747 A), ZK-5, Rho, chabazite and erionite (JP 61-254256 A), and silicoaluminophosphates (JP 02-734 A). They give better results than those on the basis of the thermodynamic equilibrium.

Mordenite has been investigated as a catalyst for methylamine production, among zeolite catalysts as mentioned above. U.S. Pat. No. 3,384,667 teaches mordenite, besides other zeolite catalysts (1968). JP 56-46846 A, JP 58-49340 A, JP 59-210050 A and JP 59-227841 A teach the use of natural or synthetic mordenites. JP 03-262540 A mentions the use of mordenite modified with silicon tetrachloride through a CVD method, in order to suppress formation of trimethylamine. There are various additional modifications by ion exchange or other methods.

Furthermore, JP 06-179640 A mentions mordenite wherein a ratio of silica to alumina is more than 10, while the ratio of silica to alumina is usually not higher than 10. JP 08-283207 A teaches rod form mordenite having aspect ratios of not less than 2, in respect to crystal form of mordenite.

There is not a large difference between zeolite and silica-alumina catalysts from a commercial point of view. Zeolite catalysts are superior to silica-alumina catalysts, because the former give dimethylamine, the most desired product, with a high selectivity. However, zeolite catalysts are inferior to silica-alumina catalysts, in respect to catalyst activity. During the practical catalyst life of one year, productivity of dimethylamine is at most a half of that using the silica-alumina catalyst. Thus, even though dimethylamine is produced with a high selectivity, the advantage and disadvantage are offset when compared in the practical productivities.

The present inventors previously applied patents (JP 11-35527 A, JP Application Nos. 10-187423, 10-180879 and 10-025832), based upon the findings that silica-modified silicoaluminophophates have a higher activity, along with a higher dimethylamine selectivity, when compared with well known zeolite catalysts and silicoaluminophosphates in the prior art. These catalysts were improved to provide a higher activity along with a higher dimethylamine selectivity, than silica-alumina catalysts, and also a superior dimethylamine productivity to that in the prior art (JP Application No. 10-293772). However, mordenites practically used as a catalyst for commercial production of methylamines are not comparable with silica-alumina catalysts, because of their lower dimethylamine productivity.

SUMMARY OF THE INVENTION

It is an object of the invention to provide mordenite catalysts for producing methylamines, which facilitate the producing process, by improving low productivity encountered by the previous mordenite catalysts, i.e., increasing dimethylamine yield per catalyst amount (STY) up to the same as or higher than that in the conventional silica-alumina catalysts, together with high dimethylamine selectivity.

The present inventors have found that mordenites of nearly spherical crystal having an aspect ratio of not higher than 2 exhibit excellent catalytic performance, against previous teachings that such mordenite is not suitable as the catalysts for production of methylamine (JP 08-283207 A). Furthermore, they have also found that mordenites containing particular elements exhibit a high dimethylamine selectivity and have a practical catalyst life with small decrease in activity along the passage of time. In addition, they are superior to silica-alimina catalysts with respect to dimethylamine STYs and productivity. Thus, the present invention has been accomplished on the basis that both a large productivity and a high dimethylamine selectivity are given to catalysts for methylamines.

The present invention relates to (1) a catalyst for producing methylamines, which comprises, as the essential component, mordenite of spherical fine particles having a crystal (single crystal) diameter of not more than 0.5 μm;

(2) a catalyst according to the item (1), in which the mordenite contains at least one element selected from the group consisting of Li, Be, Mg, La, Ce, Ca, Sr, Th, Y, Ti, Zr, V, Nb, Ta, Cr, Mn, Fe, Ru, Co, Rh, Ir, Ni, Pd, Pt, Cu, Zn, B, Ga, In, Ge and Sn;

(3) a catalyst according to the item (1), in which the mordenite contains at least one element selected from the group consisting of Ti, Y, Zr, Nb, Ta, Ga, In, Zn, Ge and Sn;

(4) a method for producing methylamines through a reaction of ammonia and methanol in the presence of the catalyst for producing methylamines according to any of the items (1) to (3) mentioned above; and (5) a method for producing methylamines, which comprises conducting a disproportionation reaction of monomethylamine in the presence of the catalyst for producing methylamines according to any of the items (1) to (3) mentioned above.

DESCRIPTION OF THE PREFERRED EMBODIMENTS

Figure 1:
FIG. 1 is a transmission electron microscope image of a catalyst 1 mentioned in Example 1 below.

Mordenites according to the present invention may be natural or synthetic ones. It may be of spherical or nearly spherical, for example, ellipsoidal form crystals. The crystal diameter is not more than 0.5 μm. The aspect ratio of such crystals corresponds to not more than 2, i.e., the crystal has almost the same sizes in the longitude and latitude. The aspect ratio of mordenites is represented by an axis ratio of c/b or c/a, wherein the axis c is that along the front view direction of the 12-membered ring micropore, and the axis b is that along the front view direction of the 8-membered ring side surface, with the axis a being the remainder. When mordenite is of spherical fine particles having a crystal diameter of not more the 0.5 μm, it is hardly detected by an electron microscope of a low magnification. Crystal size can be observed using a scanning or transmission electron microscope of 20 to 1,000 thousand magnifications. Preferable crystal diameter is from 0.05 to 0.1 μm. There is no particular limitation to the form and size of the secondary particles, i.e. aggregated crystals. The mordenites have a satisfactory catalystic life, so long as the crystal has a suitable form and size as mentioned above.

Preferably, the Si/Al ratio of the mordenites is from 5 to 10. Although this range is not limitative, too large Si/Al ratios, for example, as large as 100, result in unfavorable decrease in the conversion ratio. As for the activity, H-type mordenites are superior to Na-type ones. An amount of Na as impurity is preferably as small as possible, but an amount of not more than 2000 ppm causes no problem from a practical view point. An amount of alkali metals other than Na is preferably not more than 2000 ppm.

In order to improve the activity and selectivity, the mordenite is preferably calcined to form the H-type, after the Na or other alkali metals are exchaged with ammonium ions. Furthermore, it may preferably be modified with other suitable ions, such as Li, Be, Mg, La, Ce, Ca, Sr, Th, Y, Ti, Zr, V, Nb, Ta, Cr, Mn, Fe, Ru, Co, Rh, Ir, Ni, Pd, Pt, Cu, Zn, B, Ga, In, Ge and Sn. The ion exchange modification may be carried out by any means, for example, by immersing the mordenites in an ion solution, followed by washing with water, drying and calcination. The degree of ion exchange is preferably at least 10%, more preferably not less than 30% of the ion exchangeable capacity in mordenites.

Other methods to improve the activity and selectivity of the present mordenites include a modification by exchanging a part of the components with adequate elements through other methods than the immersion, or by coating or sedimenting adequate elements onto the mordenites. Such elements involve metals, submetals and semiconductors, including Li, Be, Mg, La, Ce, Ca, Sr, Th, Y, Ti, Nb, Ta, Zr, V, Cr, Mn, Fe, Ru, Co, Rh, Ir, Ni, Pd, Pt, Cu, Zn, B, Ga, In, Ge and Sn. Particularly, Ti, Y, Zr, Nb, Ta, Ga, In, Ge and Sn are preferred.

These elements mentioned above for modification may be contained in the mordenites in the form of simple substance atoms, oxides or double oxides. Since the mordenites are usually calcined before the catalytic usage, they are mostly present in the form of oxides, such as lithium oxide, beryllium oxide, lanthanum oxide, calcium oxide, strontium oxide, yttrium oxide, titanium oxide, niobium oxide, tantalum oxide, zirconium oxide, vanadium oxide, chromium oxide, manganese oxide, iron oxide, ruthenium oxide, cobalt oxide, rhodium oxide, iridium oxide, nickel oxide, palladium oxide, zinc oxide, copper oxide, boron oxide, gallium oxide, indium oxide, germanium oxide and tin oxide. The preferable content of the elements above in the mordenites is not more than 50% by weight, calculated as an oxide of the element, on the basis of mordenites, preferably within the range from 0.5 to 10% by weight.

The other modes for the modification are a method in which elements are mixed mechanically with mordenites, a method in which the elements are added during the course of hydrothermal synthesis, a method according to chemical vapor deposition (CVD), or a method of thermal cracking after the contact with precursors. Among them, the mechanical mixing of the oxides, or the addition of the metallic sources during the hydrothermal synthesis are particularly preferable, from view points of simplicity and steadiness.

The modification or alteration methods as described above are not critical. Any mordenites containing particular metals or oxides thereof as a part of the components fall within the scope of the invention, as long as they are prepared by exchanging, binding, sedimentation, coating, or any other process.

Mordenites are one of crystalline aluminosilicates zeolites. Zeolites such as ferrierite, epistilbite or ZSM-5 are considered to be in a series of mordenites. The zeolites have the same specific structural arrangement as mordenites, namely with respect to the secondary building units composed of the primary building unit of $AlO_4$ and $SiO_4$ tetrahedrons in the frameworks ("*Science and Application of Zeolite*", by KODANSHA Scientific). Furthermore, the regions of compositions from which crystals are formed are close each other. In the present invention, such zeolites may be used in place of the mordenites.

Synthetic mordenites used as the catalyst for producing methylamines according to the present invention may be prepared by any known methods from aluminum sources, such as aluminum sulfate, and silicon sources such as water glass. Among the mordenite catalysts for producing methylamines according to the present invention, unmodified ones are commercially available. One of examples of such mordenites is HSZ-630 HOA manufactured by TOSO KABUSHIKI KAISHA. Such commercially available mordenites can also be modified according to any method as mentioned above.

The present mordenite catalyst may be mixed with inexpensive, easily available or any suitable molecular sieves, for example, aluminosilicates or silicoaluminophosphates (SAPO) having micropore diameters of not more than 1 nm, such as chabazite, erionite, ferrierite, epistilbite, clinoptilolite, paulingite, phillipsite, levynite, zeolite-A, rho, ZK-5 and FU-1.

The present catalyst may contain, as binders, clay minerals such as kaolinite, halloysite, nacrite, montmorillonite, illite and mica. When mixed, the mordenite content in the mixtures is preferably not less than 50% by weight. The mordenite catalysts may be used as they are, or in the forms of tablets. Alternatively, compression or extrusion shaping may be applied to. They are used for a reaction of ammonia and methanol or dimethyl ether, a reaction of monomethylamine and methanol, or a conversion reaction through disproportionation of monomethylamine to dimethylamine.

These reactions mentioned above may be carried out in a gas phase fixed bed or fluidized bed, or in other flowing systems with or without nitrogen or hydrogen gas.

The production of methylamines or disproportionation reaction of monomethylamine using the catalyst according to the invention is carried out at a temperature preferably within the range from 200 to 400° C., more preferably from 250 to 350° C. The mol ratio of ammonia to methanol, N/C, in the feeding materials, is most preferably within the range from 0.5 to 2. The materials are preferably fed at a space velocity (GHSV) of 200 to 5000 $h^{-1}$. The reaction may be conducted under any pressure, namely under reduced pressure or under pressure. Preferably, it may be within the range from 0.1 to 10 MPa. The above embodiments of the present invention are not limitative.

Hereinafter, the present invention will more fully be described in reference to Examples and Comparative Examples, wherein the reaction were conducted using a flowing reaction apparatus which provides a material tank, feeding pumps, inlets for inert gas, reaction tubes (inner diameter of 13 φ, length of 300 mm, SUS 316L), a sampling tank, back pressure valves, etc. A product sample was taken over one hour, after the reaction reached the stationary state, and analyzed using a gas chromatography to measure the distribution of the product composition.

EXAMPLE 1

Material mordenite having an Si/Al ratio of 8 (HSZ-630 HOA, manufactured by TOSO KABUSHIKI KAISHA) was found to be of spherical fine particles having a crystal diameter of not more than 0.1 $\mu$m, from the observation of a transmission electron microscope (TEM) image (FIG. 1). The mordenite was shaped by compression, then pulverized and sieved to obtain a 1 to 2 mm particle size product, as Catalyst 1.

Into the reaction tube was filled 4.5 g (10 ml) of Catalyst 1. A mixture of methanol and ammonia in 1:1 weight ratio was supplied thereto at a rate of 15 g per hour and 2500 h$^{-1}$ GHSV, and a reaction was conducted under 2 MPa pressure at a temperature of 320° C. The results of the reaction after 6 hours from the start of flowing are as follows:

| Methanol conversion: | 99.2% |
|---|---|
| Selectivity: | |
| monomethylamine | 32% by weight |
| dimethylamine | 52% by weight |
| trimethylamine | 16% by weight |

EXAMPLE 2

The mordenite used in Example 1 was mixed with 5% by weight of zirconium oxide in water, and the mixture was well agitated. The mixture was dried at 110° C. overnight, and then calcined at a temperature of 600° C. for 4 hours. The resulting powder was shaped by compression, pulverized and then fractionated by sieving to obtain a 1 to 2 mm size product, as Catalyst 2. The results of the reaction under the same conditions as in Example 1 are as follows:

| Methanol conversion: | 99.2% |
|---|---|
| Selectivity: | |
| monomethylamine | 33% by weight |
| dimethylamine | 62% by weight |
| trimethylamine | 5% by weight |

Comparative Example 1

A catalyst was prepared and used for a reaction in a similar way as in Example 1, except that material mordenite in the hexagonal plate form having an Si/Al ratio of 7.5 and a crystal diameter of 1.0–3.0 $\mu$m×5.5 $\mu$m with an aspect ratio of not less than 2 (HSZ-620 HOA, manufactured by TOSO KABUSHIKI KAISHA) was used. Also, the catalyst was modified with zirconium oxide in a similar way as in Example 2. The results are shown in Table 1.

Comparative Example 2

A catalyst was prepared and used for a reaction in a similar way as in Example 1, except that material mordenite of rod form crystals having an Si/Al ratio of 9.5 and a crystal diameter of 0.1–1.3 $\mu$m×0.5 $\mu$m with an aspect ratio of 2 to 5 (HSZ-640 HOA, manufactured by TOSO KABUSHIKI KAISHA) was used. Also, the catalyst was modified with zirconium oxide in a similar way as in Example 2. The results are shown in Table 1.

Comparative Example 3

A catalyst was prepared and used for a reaction in a similar way as in Example 1, except that material mordenite of ellipsoidal crystals having an Si/Al ratio of 9 and a crystal diameter of 0.5 $\mu$m×1.0 $\mu$m with an aspect ratio of about 1 to 2 (LZM-8, manufactured by UOP) was used. Also, the catalyst was modified with zirconium oxide in a similar way as in Example 2. The results are shown in Table 1.

Comparative Example 4

A catalyst was prepared and used for a reaction in a similar way as in Example 1, except that material mordenite of rod form and spherical crystals having an Si/Al ratio is 101 and a crystal diameter of 0.6–1.4 $\mu$m×0.6 $\mu$m with an aspect ratio of not less than 2 (HSZ-690 HOA, manufactured by TOSO KABUSHIKI KAISHA) was used. Also, the catalyst was modified with zirconium oxide in a similar way as in Example 2. The results are shown in Table 1.

Comparative Example 5

A catalyst was prepared and used for a reaction in a similar way as in Example 1, except that natural mordenite having an Si/Al ratio of 9.5 and an indistinguishable crystal diameter with an aspect ratio of not less than 2, as a mixture of fibrous and rod-form crystals (#1424, manufactured by SHIN-TOHOKU KAGAKU KOGYO KABUSHI KAISHA) was used. The results are shown in Table 1.

Examples 1 and 2 and Comparative Examples 1 through 5 show that mordenite of nearly spherical fine particles having not more than 0.5 $\mu$m crystal size exhibits excellent selectivity and activity when used as it is, or after modification with an oxide. On the other side, mordenite of plate or rod form exhibits insufficient selectivity when used singly or after modification with an oxide, and is not suitable as a catalyst for producing methylamines. It has now been found that mordenite of spherical fine particles, which has heretofore been considered not to be suitable for the reaction, rather exhibits excellent performance for the reaction.

EXAMPLES 3 to 22

Catalysts were prepared in a similar way as in Example 2, except that, in place of the zirconium oxide modifier, an oxide of Si, La, Ce, Mg, Ba, Sr, Th, Y, Ti, Nb, Mn, Fe, Co, Ni, Pd, Cu, Zn, In or Sn, respectively, or kaolinite which is a typical clay mineral, is used as the respective modifier.

Into the reaction tube was filled 4.5 g (10 ml) of each catalyst. A mixture of methanol and ammonia in 1:1 weight ratio was supplied thereto at a space velocity (GHSV) of 1500 h$^{-1}$, and a reaction was conducted under 2 MPa pressure at a temperature of 300° C. The results of the reactions after 6 hours from the start of flowing are shown collectively in Table 2.

EXAMPLE 23

An aqueous sulfuric acid solution of aluminum sulfate and an aqueous water glass solution were added dropwise into an aqueous sodium chloride solution under stirring. Zirconium oxide was added thereto in such an amount as to form 5% by weight in the catalyst, and a hydrothermal synthesis was conducted at a temperature of 180 to 190° C. for 24 hours. The resulting mordenite was of nearly spherical form and had a crystal diameter of 0.1 μm with an aspect ratio of 1 to 2.

A mixture of methanol and ammonia in 1:1 weight ratio was supplied at a space velocity (GHSV) of 1500 h$^{-1}$, and the reaction was conducted at a temperature of 300° C. under 2 MPa pressure. The results of the reaction after 6 hours from the start of flowing are shown in Table 2.

EXAMPLE 24

Mordenite used in Example 1 was immersed in a copper formate dispersion in butanol (10% by weight), then taken out of the dispersion and dried. The mordenite was heated to 220° C. under 1 mmHg subatmospheric pressure for thermal decomposition of the copper formate (a kind of CVD method), thereby the copper being sedimented onto the mordenite. A catalyst was prepared in a similar way as in Example 1 and used for a reaction.

The reaction was conducted at a GHSV of 2500 h$^{-1}$ under 2 MPa pressure at a temperature of 320° C. The results of the reaction after 6 hours from the start of flowing are as follows:

| | |
|---|---|
| Methanol conversion: | 98.2% |
| Selectivity: | |
| monomethylamine | 32% by weight |
| dimethylamine | 60% by weight |
| trimethylamine | 8% by weight |

EXAMPLE 25

A synthesized H-type ZSM-5 (Si/Al ratio of 10) catalyst containing 5% by weight of zirconium oxide was prepared in a similar way as in Example 2.

A mixture of methanol and ammonia in 1:1 weight ratio was supplied at a space velocity (GHSV) of 1500 h$^{-1}$ and a reaction was conducted under 2 MPa pressure at a temperature of 300° C. The results of the reaction after 6 hours from the start of flowing are shown in Table 2.

EXAMPLE 26

Using a catalyst containing 5% by weight of kaolinite, prepared in a similar way as in Example 2, monomethylamine was supplied at a GHSV of 700 h$^{-1}$, and a disproportionation reaction of monomethylamine was conducted at a temperature of 300° C. under 2 MPa pressure to form ammonia and dimethylamine, with the results as shown in Table 3.

EXAMPLE 27

A disproportionation reaction of monomethylamine was conducted in a similar way as in Example 26, except that a catalyst containing 5% by weight of zirconium oxide was used, in place of the kaolinite, with the results of the reaction as shown in Table 3.

EXAMPLE 28

Using Catalyst 2 prepared from material mordenite of spherical fine particles having an Si/Al ratio of 8 and a crystal diameter of not more than 0.1 μm (HSZ-630 HOA, manufactured by TOSO KABUSHIKI KAISHA), a mixture of methanol and ammonia in 1:1 weight ratio was supplied at a space velocity (GHSV) of 1500 h$^{-1}$, and the reaction was continued under 2 MPa pressure at a temperature of 320° C.

After 3000 hour reaction, the methanol conversion ratio remained at 95% or more. The dimethylamine production rate at this time was 0.36 kg/L-cat.h, and no change was observed in the amine selectivity.

Comparative Example 6

Using a catalyst from hexagonal plate mordenite having an Si/Al ratio of 7.5 and a crystal diameter of 1.0–3.0 μm ×5.5 μm with an aspect ratio of not less than 2 (HSZ-620 HOA, manufactured by TOSO KABUSHIKI KAISHA), a mixture of methanol and ammonia in 1:1 weight ratio was supplied at a space velocity (GHSV) of 1500 h$^{-1}$, and a reaction was conducted under 2 MPa pressure at 320° C., with the results as shown in Table 4.

Comparative Example 7

A reaction was conducted in a similar way as in Comparative Example 6, except that a catalyst from rod-form mordenite having an Si/Al ratio of 9.5 and a crystal diameter of 0.1–1.3 μm×0.5 μm with an aspect ratio of 2 to 5 (HSZ-640 HOA, manufactured by TOSO KABUSHIKI KAISHA) was used, with the results as shown in Table 4.

Comparative Example 8

A reaction was conducted in a similar way as in Comparative Example 6, except that a catalyst from mordenite of spherical crystals having an Si/Al ratio of 9 and a crystal diameter of 0.5 μm×1.0 μm with an aspect ratio of 1 to 2 (LZM-8, manufactured by UOP) was used, with the results as shown in Table 4.

Comparative Example 9

A reaction was conducted in a similar way as in Comparative Example 6, except that a catalyst from natural mordenite composed of mixed fibrous and rod-form crystals having an Si/Al ratio of 9.5 and an indistinguishable In crystalline diameter with an aspect ratio of not less than 2 (#1424, manufactured by SHIN-TOHOKU KAGAKU KOGYO KABUSHIKI KAISHA) was used, with the results as shown in Table 4.

Comparative Example 10

Using an amorphous silica-alumina catalyst, a mixture of methanol and ammonia in 1:1 weight ratio was supplied at a space velocity (GHSV) of 1500 h$^{-1}$, and a reaction was continued under 2 MPa pressure at a temperature of 400° C. After 3000 hour reaction, the methanol conversion ratio was 99.2%. After 8000 hours, the ratio was 97.2%. Assuming that the practical life is one year or longer, the dimethylamine production rate was 0.21 kg/L-cat.h or more. The amine selectivity remained as mono-, di- and trimethylamine of 24, 25 and 51 % by weight, respectively, through the testing period.

Examples and Comparative Examples mentioned above show that the catalysts according to the present invention exhibit a high dimethylamine productivity with a lesser amount of trimethylamine, of which the demand is less, in the dimethylamine production process from methanol and ammonia or through a disproportionation reaction of methylamines. The process can be operated for longer period of time without decrease in the catalyst activity.

TABLE 1

Properties of catalysts and the results (after 6 hrs from the start of flowing)

| Examples | Catalysts | Si/Al | Crystal diameter μm | Forms | Aspect ratio | Conversion methanol (%) | Amine selectivity (wt. %) m | d | t |
|---|---|---|---|---|---|---|---|---|---|
| Ex. 1 | mordenite (Catalyst 1) | 8 | 0.05–0.1 | sphere | 1–2 | 99.2 | 32 | 52 | 16 |
| Ex. 2 | mordenite (Catalyst 2) | 8 | 0.05–0.1 | sphere | 1–2 | 99.2 | 33 | 62 | 5 |
| Comp. Ex. 1 | mordenite | 7.5 | 1.0–3.0 × 5.5 | hexagonal plate | >2 | 99.1 | 23 | 25 | 52 |
|  | Zr-modified mordenite |  |  |  |  | 98.9 | 22 | 25 | 53 |
| Comp. Ex. 2 | mordenite | 9.5 | 0.1–1.3 × 0.5 | rod | 2–5 | 99.4 | 22 | 25 | 54 |
|  | Zr-modified mordenite |  |  |  |  | 99.2 | 22 | 25 | 53 |
| Comp. Ex. 3 | mordenite | 9 | 0.5–1.0 | sphere | 1–2 | 99.2 | 22 | 25 | 53 |
|  | Zr-modified mordenite |  |  |  |  | 98.8 | 23 | 24 | 53 |
| Comp. Ex. 4 | mordenite | 101 | 0.6–1.4 × 0.6 | rod-sphere | >2 | 39.0 | 36 | 32 | 33 |
|  | Zr-modified mordenite |  |  |  |  | 37.5 | 32 | 42 | 26 |
| Comp. Ex. 5 | natural mordenite | 9.5 |  | fiber-rod | >2 | 38.0 | 69 | 28 | 3 |

Reaction conditions: temp. 320° C., pressure 2 MPa, and GHSV 2500 h$^{-1}$
In the amine selectivity,
m: monomethylamine
d: dimethylamine
t: trimethylamine

TABLE 2

Results from modified mordenites (reaction of methanol and ammonia)

| | Molecular sieves | Modifiers | Amount added (wt. %) | Methanol conversion ratio (%) | Amine selectivity (wt. %) m | d | t |
|---|---|---|---|---|---|---|---|
| Ex. 3 | mordenite | silica powder | 5 | 98.6 | 32 | 56 | 12 |
| Ex. 4 | mordenite | lanthanum oxide | 5 | 95.5 | 33 | 60 | 7 |
| Ex. 5 | mordenite | cerium oxide | 5 | 94.4 | 33 | 60 | 7 |
| Ex. 6 | mordenite | mangnesium oxide | 5 | 86.1 | 33 | 59 | 8 |
| Ex. 7 | mordenite | barium oxide | 5 | 92.1 | 36 | 57 | 7 |
| Ex. 8 | mordenite | strontium oxide | 5 | 93.8 | 33 | 62 | 5 |
| Ex. 9 | mordenite | thorium oxide | 5 | 93.1 | 33 | 60 | 7 |
| Ex. 10 | mordenite | yttrium oxide | 5 | 93.5 | 35 | 60 | 5 |
| Ex. 11 | mordenite | titanium oxide | 5 | 98.0 | 35 | 61 | 4 |
| Ex. 12 | mordenite | niobium oxide | 5 | 96.0 | 33 | 60 | 7 |
| Ex. 13 | mordenite | manganese oxide | 5 | 97.0 | 32 | 59 | 9 |
| Ex. 14 | mordenite | iron oxide | 5 | 98.1 | 36 | 59 | 5 |
| Ex. 15 | mordenite | cobalt oxide | 5 | 94.1 | 32 | 59 | 9 |
| Ex. 16 | mordenite | nickel oxide | 5 | 96.6 | 33 | 60 | 7 |
| Ex. 17 | mordenite | palladium oxide | 5 | 97.0 | 33 | 61 | 6 |
| Ex. 18 | mordenite | copper(I) oxide | 5 | 95.1 | 32 | 58 | 10 |
| Ex. 19 | mordenite | zinc oxide | 5 | 78.1 | 40 | 58 | 2 |
| Ex. 20 | mordenite | indium oxide | 5 | 96.6 | 32 | 62 | 6 |
| Ex. 21 | mordenite | tin(IV) oxide | 5 | 96.2 | 32 | 61 | 7 |
| Ex. 22 | mordenite | kaolinite | 5 | 97.6 | 35 | 60 | 5 |
| Ex. 23 | mordenite | zirconium oxide | 5 | 97.4 | 33 | 59 | 8 |
| Ex. 25 | ZSM-5 | zirconium oxide | 5 | 97.6 | 29 | 38 | 33 |
| Comp. Ex. 10 | silica-alumina | zirconium oxide |  | 99.6 | 24 | 25 | 51 |

Reaction conditions: temp. 300° C. (Comp. Ex. 10, 400° C.), pressure 2 MPa, and GHSV 1500 hr$^{-1}$
Mordenite: HSZ630 HOA (manufactured by TOSO K.K.)
In the amine selectivity,
m: monomethylamine

TABLE 2-continued

Results from modified mordenites (reaction of methanol and ammonia)

| Molecular sieves | Modifiers | Amount added (wt. %) | Methanol conversion ratio (%) | Amine selectivity (wt. %) | | |
|---|---|---|---|---|---|---|
| | | | | m | d | t | d: dimethylamine
t: trimethylamine

TABLE 3

Results from modified mordenites (disproportionation reaction of monomethylamine)

| | Molecular sieves | Modifiers | Amount added (wt. %) | Monomethylamine conversion (%) | Amine selectivity | |
|---|---|---|---|---|---|---|
| | | | | | d | t |
| Ex. 26 | mordenite | kaolinite | 5 | 82.6 | 88 | 12 |
| Ex. 27 | mordenite | zirconium oxide | 5 | 80.5 | 91 | 9 |

Reaction conditions: Temp. 300° C., pressure 2 MPa, and GHSV 700 hr$^{-1}$
Mordenite: HSZ630 HOA (from TOSO K.K.)
In the amine selectivity,
d: dimethylamine
t: trimethylamine

TABLE 4

Catalyst activity and dimethyamine productivity

| Examples | Catalysts | Crystal diameter μm | Forms | Methanol conversion ratio (%) | | | Dimethylamine selectivity STY Kg/L-cat.h |
|---|---|---|---|---|---|---|---|
| | | | | 6 h | 1500 h | 3000 h | |
| Ex. 28 | Catalyst 2 | 0.05–0.1 | sphere | 98.9 | 97.4 | 95.8 | 0.36 |
| Comp. Ex. 6 | mordenite (HSZ-620 HOA) | 1.0–3.0 × 5.5 | hexagonal plate | 99.1 | 94.8 | 90.2 | 0.13 |
| Comp. Ex. 7 | mordenite (HSZ-640 HOA) | 0.1–1.3 × 0.5 | rod | 99.4 | 95.4 | 92.4 | 0.14 |
| Comp Ex. 8 | mordenite (UOP LZM-8) | 0.5 × 1.0 | sphere | 99.2 | 96.2 | 94.1 | 0.15 |
| Comp. Ex. 9 | mordenite (SHIN-TOHOKU K.K.) | (unknown) | fiber-rod | 47.2 | — | — | 0.05 |
| Comp. Ex. 10 | silica-alumina | | | 99.6 | 99.4 | 99.2 | 0.21 |

Reaction conditions: temp. 320° C. (Comp. Ex. 10, 400° C.), pressure 2 MPa, and GHSV 1500 hr$^{-1}$

What is claimed is:

1. A catalyst for producing methylamines which comprises, as the essential components, mordenite and at least one element selected from the group consisting of Li, Be, Mg, La, Ce, Ca, Sr, Th, Y, Ti, Zr, V, Nb, Ta, Cr, Mn, Fe, Ru, Co, Rh, Ir, Ni, Pd, Pt, Cu, Zn, B, Ga, In, Ge and Sn, said mordenite being fine particles which are spherical or nearly spherical having an aspect ratio of not more than 2 and have a crystallite diameter of not greater than 0.5 μm.

2. A catalyst for producing methylamines which comprises, as the essential components, mordenite and at least one element selected from the group consisting of Ti, Y, Zr, Nb, Ta, Ga, In, Zn, Ge and Sn, said mordenite being fine particles which are spherical or nearly spherical having an aspect ratio of not more than 2 aspect ratio and have a crystallite diameter of not greater than 0.5 μm.

3. A method for producing methylamines which comprises allowing ammonia to react with methanol in the presence of a catalyst for producing methylamines, said catalyst comprising, as the essential component, fine particles of mordenite which are spherical or nearly spherical having an aspect ratio of not more than 2 and have a crystallite diameter of not greater than 0.5 μm.

4. A method for producing methylamines which comprises allowing ammonia to react with methanol in the presence of a catalyst for producing methylamines, said catalyst comprising, as the essential components, mordenite and at least one element selected from the group consisting of Li, Be, Mg, La, Ce, Ca, Sr, Th, Y, Ti, Zr, V, Nb, Ta, Cr, Mn, Fe, Ru, Co, Rh, Ir, Ni, Pd, Pt, Cu, Zn, B, Ga, In, Ge and Sn, said mordenite being fine particles which are spherical or nearly spherical having an aspect ratio of not more than 2 and have a crystallite diameter of not greater than 0.5 1 μm.

5. A method for producing methylamines which comprises allowing ammonia to react with methanol in the presence of a catalyst for producing methylamines, said catalyst comprising, as the essential components, mordenite and at least one element selected from the group consisting of Ti, Y, Zr, Nb, Ta, Ga, In, Zn, Ge and Sn, said mordenite being fine particles which are spherical or nearly spherical having an aspect ratio of not more than 2 and have a crystallite diameter of not greater than 0.5 μm.

6. A method for producing methylamines which comprises conducting a disproportionation reaction of monomethylamine in the presence of a catalyst for producing methylamines, said catalyst comprising, as the essential component, particles of mordenite which are spherical or nearly spherical having an aspect ratio of not more than 2 and have a crystallite diameter of not greater than 0.5 μm.

7. A method for producing methylamines which comprises conducting a disproportionation reaction of monomethylamine in the presence of a catalyst for producing methylamines, said catalyst comprising, as the essential components, mordenite and at least one element selected from the group consisting of Li, Be, Mg, La, Ce, Ca, Sr, Th, Y, Ti, Zr, V, Nb, Ta, Cr, Mn, Fe, Ru, Co, Rh, Ir, Ni, Pd, Pt, Cu, Zn, B, Ga, In, Ge and Sn, said mordenite being fine particles which are spherical or nearly spherical having an aspect ratio of not more than 2 and have a crystallite diameter of not greater than 0.5 μm.

8. A method for producing methylamines which comprises conducting a disproportionation reaction of monomethylamine in the presence of a catalyst for producing methylamines, said catalyst comprising, as the essential components, mordenite and at least one element selected from the group consisting of Ti, Y, Zr, Nb, Ta, Ga, In, Zn, Ge and Sn, said mordenite being fine particles which are spherical or nearly spherical having an aspect ratio of not more than 2 and have a crystallite diameter of not larger than 0.5 μm.

* * * * *